US011687577B2

(12) United States Patent
Kivatinos et al.

(10) Patent No.: US 11,687,577 B2
(45) Date of Patent: Jun. 27, 2023

(54) IDENTIFYING MISSING QUESTIONS BY CLUSTERING AND OUTLIER DETECTION

(71) Applicant: drchrono Inc., Sunnyvale, CA (US)

(72) Inventors: Daniel Kivatinos, Mountain View, CA (US); Michael Nusimow, Mountain View, CA (US); Martin Borgt, Sunnyvale, CA (US); Soham Waychal, Sunnyvale, CA (US)

(73) Assignee: DRCHRONO INC., Sunnyvale, CA (US)

( * ) Notice: Subject to any disclaimer, the term of this patent is extended or adjusted under 35 U.S.C. 154(b) by 1034 days.

(21) Appl. No.: 16/457,794

(22) Filed: Jun. 28, 2019

(65) Prior Publication Data
US 2020/0034366 A1    Jan. 30, 2020

Related U.S. Application Data
(60) Provisional application No. 62/703,879, filed on Jul. 27, 2018.

(51) Int. Cl.
| | | |
|---|---|---|
| *G06F 16/24* | (2019.01) | |
| *G06F 16/35* | (2019.01) | |
| *G06F 16/2455* | (2019.01) | |
| *G06F 16/28* | (2019.01) | |
| *G06N 3/084* | (2023.01) | |
| *G16H 10/60* | (2018.01) | |
| *G06N 20/20* | (2019.01) | |
| *G06N 20/10* | (2019.01) | |
| *G06F 18/23213* | (2023.01) | |
| *G06F 18/2413* | (2023.01) | |
| *G06N 3/045* | (2023.01) | |

(52) U.S. Cl.
CPC ........ *G06F 16/35* (2019.01); *G06F 16/24556* (2019.01); *G06F 16/285* (2019.01); *G06F 18/23213* (2023.01); *G06F 18/24147* (2023.01); *G06N 3/045* (2023.01); *G06N 3/084* (2013.01); *G06N 20/10* (2019.01); *G06N 20/20* (2019.01); *G16H 10/60* (2018.01)

(58) Field of Classification Search
CPC ..................................................... G06F 16/24
USPC ........................................................ 706/25
See application file for complete search history.

(56) References Cited

U.S. PATENT DOCUMENTS

| | | | | |
|---|---|---|---|---|
| 2020/0242506 | A1* | 7/2020 | Kelly | G06N 3/088 |
| 2020/0304804 | A1* | 9/2020 | Habibian | G06N 3/0454 |
| 2020/0342310 | A1* | 10/2020 | Farchi | G06N 20/10 |
| 2020/0356591 | A1* | 11/2020 | Yada | G06F 16/5862 |

* cited by examiner

*Primary Examiner* — Nga B Nguyen
(74) *Attorney, Agent, or Firm* — James J. DeCarlo; Greenberg Traurig, LLP

(57) ABSTRACT

A machine learning system may be used to suggest clinical questions to ask during or after a patient appointment. A first encoder may encode information and a second encoder may encode second information related to the current patient appointment. An aggregate encoding may be generated using the encoded first information and encoded second information. The current patient appointment may be clustered with similar appointments based on the aggregate encoding. Outlier analysis may be performed to determine if the appointment is an outlier, and, if so, which features contribute the most to outlier status. The system may generate one or more questions to ask about the features that contribute the most to outlier status.

28 Claims, 4 Drawing Sheets

IDENTIFYING MISSING QUESTIONS BY CLUSTERING AND OUTLIER DETECTION

CROSS-REFERENCE TO RELATED APPLICATIONS

This application claims the benefit of U.S. Provisional Patent Application No. 62/703,879, filed Jul. 27, 2018, which is hereby incorporated by reference in its entirety.

FIELD OF THE INVENTION

The present invention relates to a computer system and method for using machine learning to identify questions that a practitioner may have neglected to ask during a patient appointment.

BACKGROUND

Health practitioners see patients in appointments and record information collected during the appointment in clinical notes. Appointments may be in person or virtual. The clinical notes may include a variety of information including information about everything that occurred during the appointment, such as any procedures that were performed, the medications the patient is taking, the diagnoses made, and so on.

One problem faced by practitioners is that they may inadvertently forget to ask the patient for important information before the patient leaves the appointment. This can lead to significant inefficiency if the practitioner is unable to adequately treat the patient based on the provided information or if the practitioner cannot submit the necessary information to the payer, such as a health insurance company, without the additional information. It may become necessary for the practitioner to require the patient to make another appointment to fill in the necessary information.

SUMMARY OF THE INVENTION

Some embodiments relate to a machine learning system for recommending one or more clinical questions to ask during or after a patient appointment. Recommended clinical questions may help ensure that practitioners have all the information needed for treatment of the patient, all the information needed for submission of a claim to the payer, and for other reasons.

In some embodiments, a first encoder is trained to encode information of a first type into a first vector representation. A second encoder is trained to encode information of a second type into a second vector representation. More or fewer encoders may be used. A set of medical records of patient appointments is provided. First portions of information of the first type and second portions of information of the second type may be extracted from the medical records. The first portions of information may be encoded by the first encoder and the second portions of information may be encoded by the second encoder. For each medical record, an aggregator may aggregate the first portion of information and second portion of information to generate an aggregate encoding. The medical records may be clustered based on the aggregate encoding or the encoded first portions of information and encoded second portions of information.

In some embodiments, an input medical record is provided. Third portion of information of the first type and fourth portion of information of the second type may be extracted from the input medical record. The third portion of information may be encoded by the first encoder, and the fourth portion of information may be encoded by the second encoder. The encoded third portion of information and encoded fourth portion of information may be aggregated by the aggregator to generate an aggregate encoding of the input medical record. The input medical record may be mapped to the space of existing medical record clusters based the its aggregate encoding or the encoded third portion of information and encoded fourth portion of information.

In some embodiments, it is determined whether the input medical record is an outlier of a cluster. If it is, then it is determined which of the features of the input medical record cause it to be an outlier, and one or more questions may be generated about those features.

DETAILED DESCRIPTION

Figure 1:
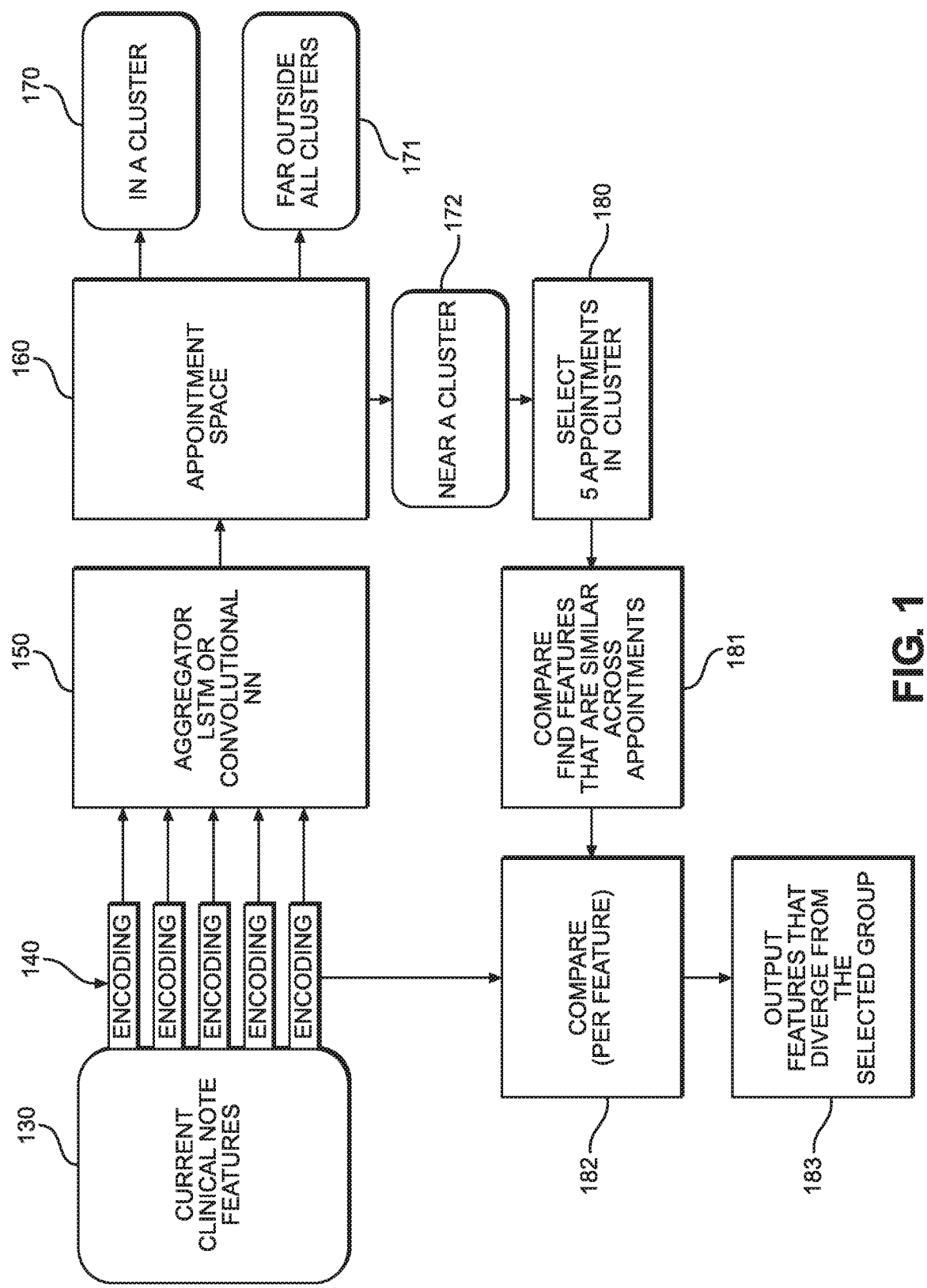
FIG. 1 illustrates an exemplary missing question identification system.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

FIG. 1 illustrates an exemplary missing question identification system 100, which uses machine learning to assess where a practitioner has forgotten to ask a question that is commonly asked in similar types of appointments. The missing question identification system 100 is implemented using computer software and hardware. The missing question identification system 100 may comprise one computer system or multiple computer systems operating in coordination over a network or other communication channel.

Embodiments may be used to recommend one or more questions for a practitioner to ask during or after a patient appointment. Patient appointments may occur in-person at a practitioner's office or may occur virtually, such as by video conference. During a patient appointment, practitioners commonly record information in a clinical note. The clinical note need not comprise just text and notes but may comprise a variety of information such as patient problems/diagnoses, medications, medical procedures, procedure codes, fee codes, billing codes, diagnosis codes, allergies, lab tests, reasons for the visit, prescribed drugs, patient vitals such as height and weight, and so on.

In the missing question identification system 100, a clinical note is provided for a current appointment. Clinical note relates to the patient's current appointment and has clinical note features 130. The clinical note features 130 may include patient problems/diagnoses, medications, medical procedures, procedure codes, fee codes, billing codes, diagnosis codes, allergies, lab tests, reasons for the visit, prescribed drugs, patient vitals such as height and weight, and so on. Each of these forms of information may be encoded by separate encoders to generate encodings 140 for each type of information. In some embodiments, the encoders are implemented with neural networks. The encoders may be referred to as *2Vec algorithms, such as Procedures2Vec, Problems2Vec, RX2Vec, and so forth, because they may be implemented using similar procedures to Word2Vec, an algorithm for mapping words to vector representations.

An appointment transcript comprising a transcript of the appointment or free text notes from practitioner may be provided. An information retrieval algorithm may be performed on the appointment transcript to extract semantic information. For example, term frequency-inverse document frequency (TF-IDF) or Latent Dirichlet Allocation (LDA) may be performed on the appointment transcript to generate keywords and topics for the appointment transcript.

Past clinical appointments may be clustered using an unsupervised machine learning clustering algorithm, such as k-means clustering. The clustering may be performed based on the information encoded by encoders, such as encoded information about patient problems/diagnoses, medications, medical procedures, procedure codes, fee codes, billing codes, diagnosis codes, allergies, lab tests, reasons for the visit, prescribe drugs, patient vitals such as height and weight, and so on. The clustering may also be performed based on the semantic information extracted from the appointment transcript in the form of keywords and topics.

In an embodiment, the encoded information and semantic information are aggregated into a single aggregate encoding. Aggregator 150 may be implemented with a Long Short-Term Memory (LSTM) Neural Network or Convolutional Neural Network (CNN). The aggregator 150 may aggregate the encodings 140 into an aggregate encoding. The aggregate encoding is a vector in an appointment space 160. The appointment space is vector space where points in the space represent appointments. Clustering may then be performed based on the aggregate encodings, where there is a single aggregate encoding per past appointment. The performance of the clustering may be improved by combining a plurality of encodings and semantic information into a single aggregate representation, rather than clustering directly on the plurality of encodings and semantic information. The aggregation may be helpful to reduce dimensionality so that clustering may be more effective When a new input appointment is provided, the input appointment may be run through processes at steps 130, 140, 150, and 160 to extract and encode information of various types and also extract keywords and topics using information retrieval. The new input appointment is then mapped into the appointment space 160 based on its aggregate encoding. It is determined whether the new input is in a cluster 170, far outside all clusters 171, or near a cluster 172. If the new input appointment is in a cluster 170 or far outside all clusters 171, then the process may end.

If the new input appointment is near a cluster 172, then it may be determined that the new input appointment is an outlier from the cluster.

If it is determined that the new input appointment is an outlier, then the system identifies the feature that is causing the most error. For example, the feature may be, for example, a lack of information about a particular medication, test, or procedure.

In an embodiment, the system selects a plurality of appointments in the cluster (step 180). In particular, these are aggregate encodings of the appointments. In an embodiment, five appointments may be selected at random from the cluster. In step 181, the plurality of appointments are compared to determined what features they have that are similar between appointments and which features are different between the appointments. For example, features may be patient problems/diagnoses, medications, medical procedures, procedure codes, fee codes, billing codes, diagnosis codes, allergies, lab tests, reasons for the visit, prescribed drugs, patient vitals such as height and weight, and so on. The features of the appointments are iterated over to determine for each feature whether all the appointments have a similar value or if any appointment has a different value.

Similarity may be measured for features of the appointments, and for other aspects herein, by using a distance metric. The features of the appointments may be represented as encodings 140 created by inputting the features into an encoder, such as an encoder neural network. The encodings may be vectors. Vectors that are closer than a threshold distance in the vector space may be considered close and vectors that are farther than a threshold distance in the vector space made be considered dissimilar. Distance metrics that may be used to measure similarity include dot product and cosine similarity between vectors.

Features that are similar between the features selected from the cluster may be considered to be representative of features in the cluster. The system may then determine whether the new input appointment has features that differ from these representative features (step 182). For each feature determined to be a representative feature in step 181, the value of the feature in new input appointment may be compared against the values of the feature in the selected plurality of appointments from the cluster or a statistic, such as mean or median, computed thereon. Similarity between the value of the feature in the input new appointment and the representative features may be determined. In an embodiment, similarity is determined by measuring the distance between the vectors representing the encodings of the features in the input new appointment and the vectors representing the encodings of the representative features, such as by using cosine similarity or dot product. The features of the new input appointment that are dissimilar to the representative features of the selected plurality of appointments are areas that cause the input new appointment to be an outlier. Therefore, the system may then generate a prompt to the practitioner to ask the patient about the outlier features (step 183).

Figure 2A:
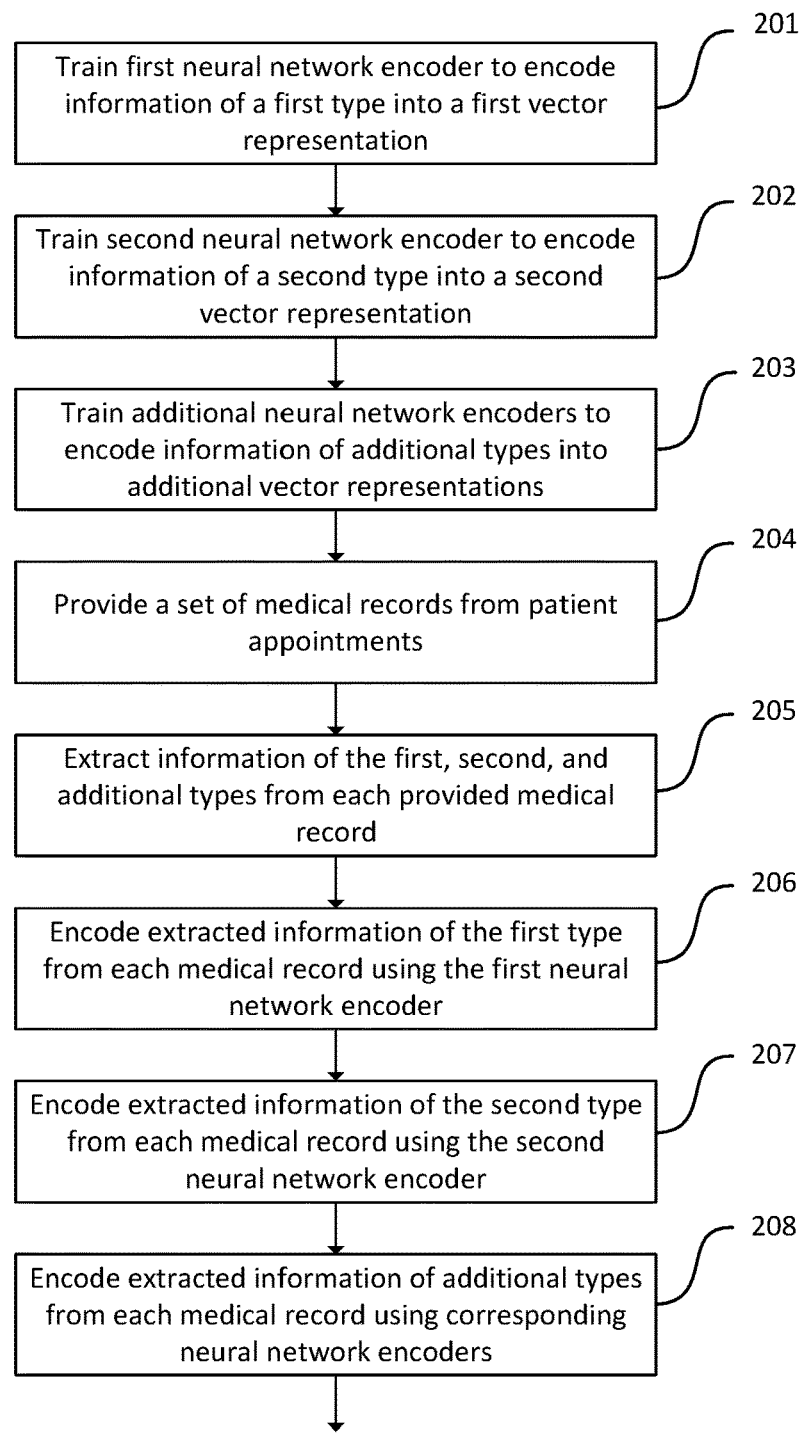
FIGS. 2A-C illustrates an exemplary method for identifying missing questions.
Figure 2B:
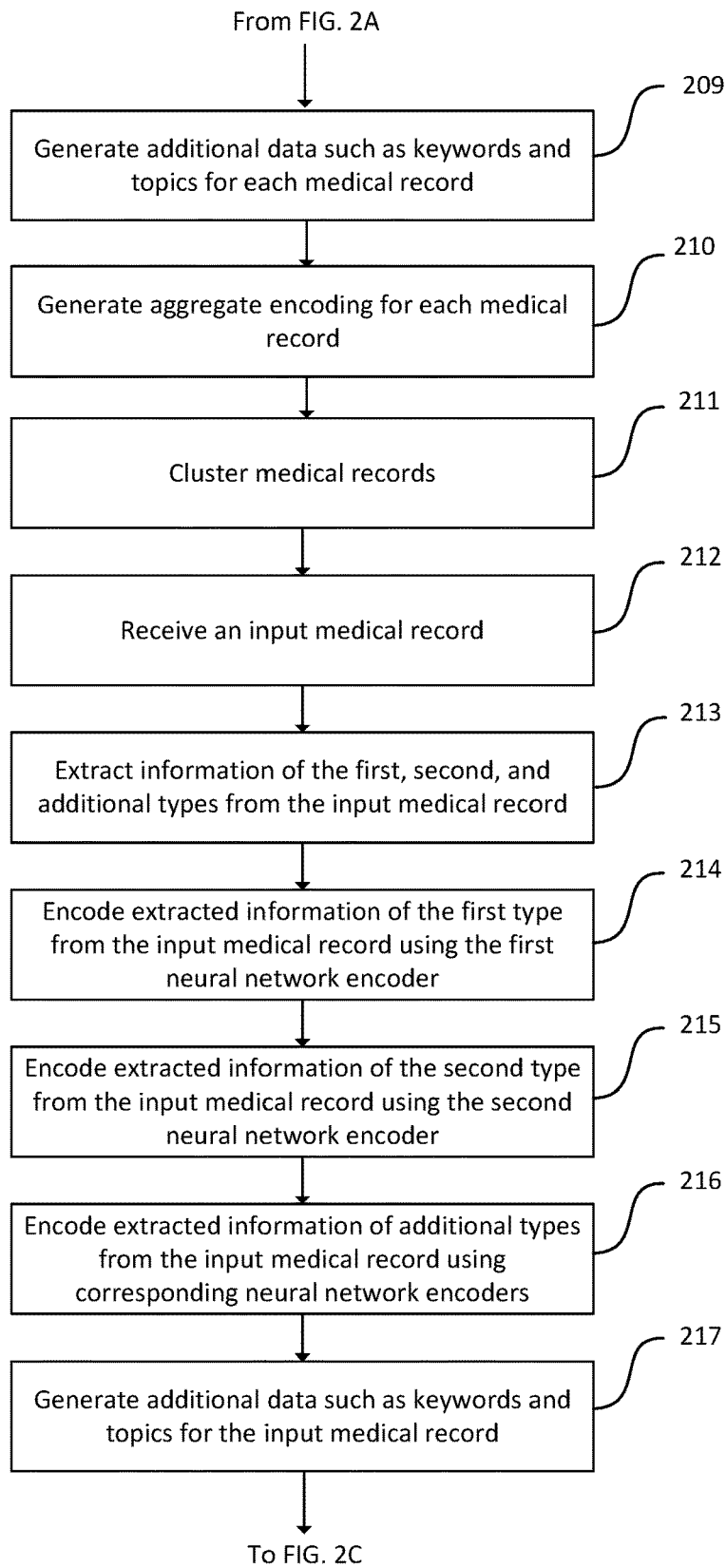
Figure 2C:
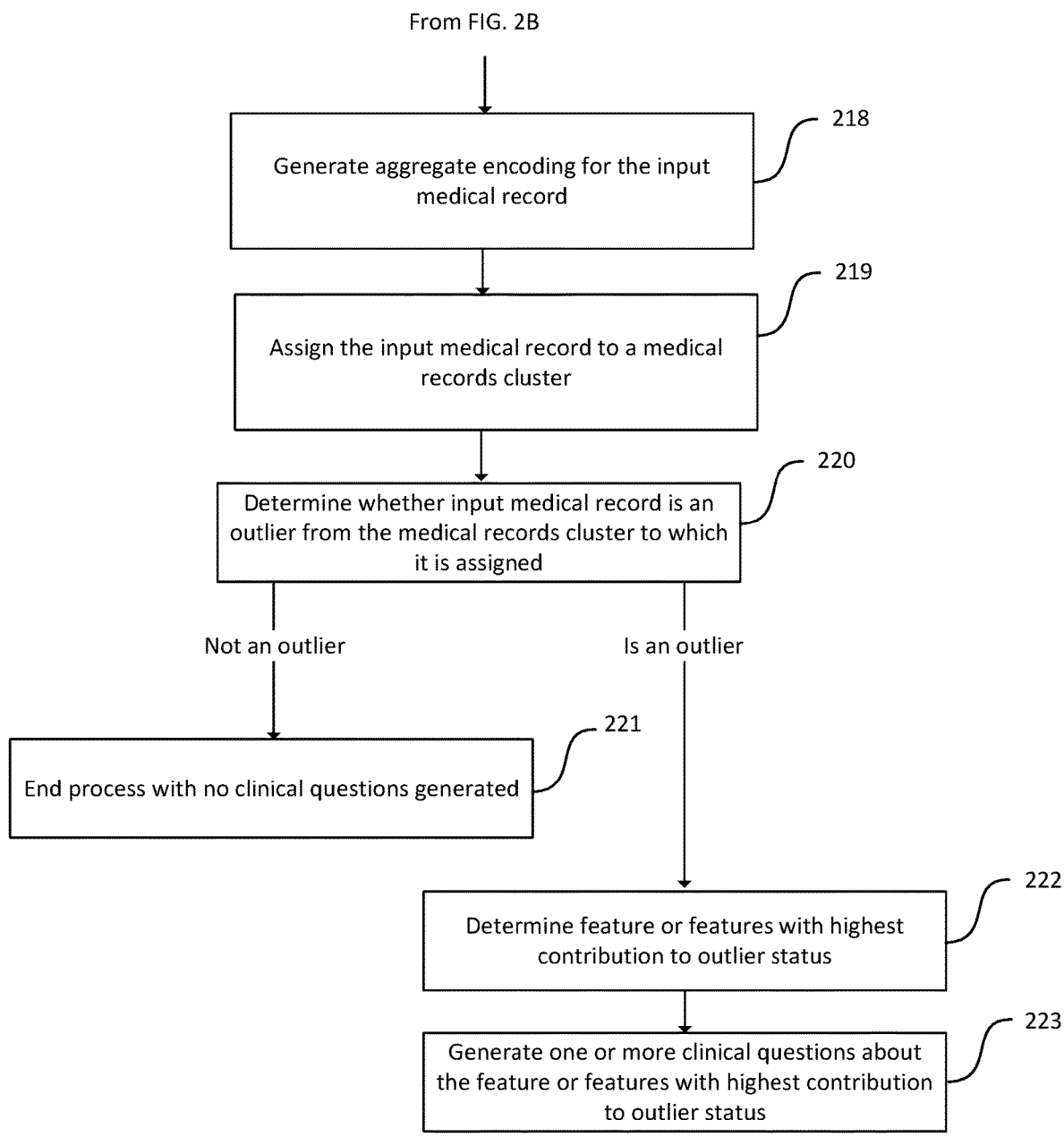

FIGS. 2A-C illustrate an exemplary method 200 for using missing question identification system 200. In step 201, a first neural network encoder is trained to encode information of a first type into a first vector representation. A neural network encoder is an encoder that is implemented with one or more neural networks.

The encoding of the input to the vector representation may be used to relate inputs that are similar. For example, inputs that are similar may be mapped by the encoder to vectors that are close together in vector space, while inputs that are dissimilar may be mapped to vectors that are far apart in vector space. Vector distance may be measured by a number of metrics, one of which is cosine similarity and another of which is dot product.

One form of encoder that may be used for the first neural network encoder, and other encoders herein, is a neural network autoencoder. A neural network autoencoder is an autoencoder that is implemented with one or more neural networks. An autoencoder comprises an encoder and a decoder. The encoder accepts an input and outputs a vector representation. The decoder accepts the vector representation as input and outputs an output vector. The autoencoder is trained to produce an output vector that is the same as the input vector. The compression of the input vector to an intermediate vector representation means that the output vector may not be identical to the input vector. However, the training process for the autoencoder aims to reduce the vector distance between the output vector and the initial input to the encoder component of the autoencoder.

In an autoencoder, the intermediate vector representation between the encoder and decoder may be used as an encoding or embedding of the input. The vector representation commonly compresses the input to a lower-dimensional vector space.

A variational autoencoder is one type of autoencoder that may be used herein to implement the autoencoders. In a variational autoencoder, the Kullback-Leibler divergence may be used in the loss function for training the autoencoder. The loss function based on Kullback-Leibler divergence effectively encourages the encoder to distribute encodings evenly around the center of the vector space. The loss function penalizes the encoder if it attempts to cluster the encodings in specific regions, away from the origin.

As an alternative to a variational autoencoder, some embodiments may use a sequence-to-sequence (Seq2Seq) encoder-decoder. A Seq2Seq encoder-decoder includes a Seq2Seq encoder and Seq2Seq decoder. The Seq2Seq encoder treats codes as a sentence and encodes them together to create a concise encoding of the list of codes together. This allows encoding a sequence of inputs into a vector representation and mapping the vector representation back into a sequence using the Seq2Seq decoder. Seq2Seq encoders and decoders may be implemented with neural networks that map from sequences of inputs to a vector. Such neural networks may include recurrent neural networks (RNNs) and long short-term memory (LSTM) neural networks.

In step 202, a second neural network encoder is trained to encode information of a second type into a second vector representation. This may be an autoencoder, variational autoencoder, Seq2Seq encoder-decoder, and so on.

In step 203, additional neural network encoders may be trained to encode information of additional types into vector representations. This process may be continued for three, four, five, or more types of information until neural network encoders are trained to encode all of the desired information from records of past medical appointments. Typically a different neural network encoder will be used for each different type of information. For example, billing codes will be encoded by one neural network and diagnosis codes will be encoded by a separate neural network. Likewise, for medications, lab tests, and so on.

In step 204, a set of medical records of past patient appointments is provided. These appointments may be across many different patients and practitioners.

In step 205, a first portion of information of a first type and a second portion of information of a second type is extracted from each of the medical records. An additional plurality of portions of information of other types may also be extracted from the medical records, such as a third information of a third type, fourth information of a fourth type, and so on.

In step 206, for each of the medical records, the first portions of information are input to the first neural network to output encoded first portions of information In step 207, for each of the medical records, the second portions of information are input to the second neural network to output encoded second portions of information In step 208, additional portions of information from the medical records may be input to separate neural networks per type to output encoded representations of each portion of information.

In step 209, for each of the medical records, information retrieval methods may be performed to generate semantic information, such as keywords and topics.

In step 210, for each of the medical records, the first encoded portions of information, second encoded portions of information, and additional encoded portions of information and the semantic information may be aggregated into an aggregate encoding. Each of these components may be input to an aggregator. The aggregator performs aggregation of the encodings and other information about the appointment and outputs a single aggregate vector representation. The aggregate vector representation is a vector in a vector space representing appointments, which may be referred to as the appointment space. The aggregator may be a machine learning model such as an RNN, LSTM, or convolutional neural network (CNN). The aggregator is trained to output similar vector encodings when the underlying appointments were similar, and to output dissimilar vector encodings when the appointments were different. Similarity between vectors may be evaluated using a distance metric like cosine similarity or the dot product.

In an embodiment, training examples for the aggregator are obtained by identifying similar appointments and using these as positive examples, and finding dissimilar appointments and using these as negative examples. The system may identify similar appointments by finding appointments where similar clinical questions were asked. Similarity between clinical questions may be measured by encoding the clinical questions and measuring vector distance, such as by cosine similarity or dot product. Vectors that are close are similar, and those that are far apart are dissimilar. The aggregator is trained to output a similar encoding for similar appointments and to output dissimilar encodings for dissimilar appointments. In an embodiment, training is performed using the Triplet Loss Function. The Triplet Loss Function trains by using three examples: an anchor, a positive, and a negative. The Triplet Loss Function trains the anchor and the positive to have similar encodings, and trains the anchor and the negative to have different encodings.

In an embodiment, the aggregator is implemented using an LSTM. The LSTM may be trained accept a variable length sequence of encodings and output a hidden state. The hidden state of the LSTM after all of the encodings have been input may comprise the output encoding of the aggregator. In the training process using the Triplet Loss Function, the encodings of the anchor example may be input into a first copy of the LSTM and the encodings of the positive may be input into a second copy of the LSTM. The resulting outputs may then be compared using the Triplet Loss Function, and backpropagation is applied to adjust the weights of the LSTM to make the outputs more similar. A similar process is applied for an anchor and a negative example, except that the Triplet Loss Function and backpropagation are applied to adjust the weights of the LSTM to make the output vectors farther apart.

In an embodiment, the aggregator is implemented using a CNN. In a CNN, neural network nodes are connected in to neural network nodes in subsequent layers in only a local area around the node. That is, neural network nodes are not connected to other nodes that are far away from them in the subsequent layer. A CNN may have a plurality of layers that apply different convolutional kernels, also known as filters. In the training process using the Triplet Loss Function, the encodings of the anchor example may be input into a first copy of the CNN and the encodings of the positive may be input into a second copy of the CNN. The resulting outputs may then be compared using the Triplet Loss Function, and backpropagation is applied to adjust the weights of the CNN to make the outputs more similar. A similar process is applied for an anchor and a negative example, except that the Triplet Loss Function and backpropagation are applied to adjust the weights of the CNN to make the output vectors farther apart.

In step 211, the medical records are clustered using a machine learning clustering algorithm, such as k-means clustering. In one embodiment, the clustering is performed based on the aggregate encodings. In an embodiment, the clustering is performed based on the first and second encoded portions of information and any additional encoded portions of information and the keywords and topics.

In step 212, an input medical record is provided.

In step 213, a third portion of information of the first type and a fourth portion of information of the second type are extracted from the input medical record.

In step 214, the third portion of information is input to the first neural network to output an encoded third portion of information.

In step 215, the fourth portion of information is input to the second neural network to output an encoded fourth portion of information.

In step 216, additional portions of information from the input medical record may be input to separate neural networks per type to output encoded representations of each portion of information.

In step 217, information retrieval methods may be performed to generate keywords and topics for the input medical records In step 218, the encoded third portion of information, encoded fourth portion of information, and additional encoded portions of information and the semantic information may be aggregated into an aggregate encoding. Each of these components may be input to the aggregator. The aggregator performs aggregation of the encodings and other information about the appointment and outputs a single aggregate vector representation. This aggregate vector representation is an encoding in the appointment vector space.

In step 219, the input medical record is mapped to the cluster that it is closest to in the appointment vector space. In one embodiment, finding the nearest cluster is performed based on the aggregate encodings. In an embodiment, finding the nearest cluster is performed based on the first and second encoded portions of information and any additional encoded portions of information and the keywords and topics. In an embodiment, the input medical record is determined to be either in a cluster, near a cluster, or far from all clusters.

In step 220, it is determined whether the input medical record is an outlier from the medical records cluster into which it was clustered. In an embodiment, this is determined when the input medical record is located near a cluster without being in the cluster. Meanwhile, if the input medical record is in the cluster or far from all clusters, then it may be determined that it is not an outlier of a particular cluster.

In some embodiments, the determination of whether the input medical record is an outlier is performed by using the z-score, which represents the number of standard deviations the value is from the mean—in this case the cluster centroid. In some embodiments, the determination of whether the input medical record is an outlier is performed by using Density-based Spatial Clustering of Applications with Noise (DBSCAN), which identifies outliers as those points that occupy low-density regions—specifically regions with few other points. In some embodiments, the determination of whether the input medical record is an outlier is performed by randomly sampling a plurality of appointments in the cluster and comparing each of the plurality of appointments with the input medical record. When the input medical record is very different from the sampled plurality of appointments, then it is determined that the input medical record is an outlier. When the input medical record is not very different from the sample plurality of appointments, then it is determined that the input medical record is not an outlier. The similarity or difference may be measured by taking the vector distance between the encoded versions of the appointments, such as by cosine similarity or dot product.

In step 221, if the input medical record is not an outlier, then the process stops and no clinical question is generated.

In step 222, if it is determined that the input medical record is an outlier, then the system may determine the one or more features that contribute most highly to the input medical record being an outlier.

In an embodiment, determining which features cause the input medical record to be an outlier is performed by selecting a subset of the appointments in the cluster and identifying what features they have that are similar and what features they have that are different. As described previously, the features that are similar across appointments may be treated as representative of the cluster. These representative features may then be compared to the corresponding features of the input medical record. Where there are differences, the features of the input medical record are considered to be outliers.

In some embodiments, step 222 is performed by iterating through each feature, such as demographics, problem, procedure, medications, and transcript, and comparing the distance of each feature to the centroid. Features greater than a threshold distance from the centroid may be flagged as contributing to outlier status and needing further analysis.

In some embodiments, the determination of which features contribute most highly to the outlier status, is performed by using an attention algorithm. The attention algorithm accepts as input the patient and practitioner background, prior visits, and current information from the clinical note, and the attention algorithm outputs additional information that requires further analysis.

In step 223, after the features that contributed most to outlier status are identified, the system may generate one or more clinical questions about the feature. In some embodiments, the questions may be a prompt for the doctor to ask about a specific feature, such as asking about missing lab tests or medications that the patient should have obtained. In some embodiments, the questions may be generated based on a template, with the topic of the question filled in based on the features identified in step 222.

The terminology used herein is for the purpose of describing particular aspects only and is not intended to be limiting of the disclosure. As used herein, the singular forms "a," "an," and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been particularly shown and described with reference to specific embodiments thereof, it should be understood that changes in the form and details of the disclosed embodiments may be made without departing from the scope of the invention. Although various advantages, aspects, and objects of the present invention have been discussed herein with reference to various embodiments, it will be understood that the scope of the invention should not be limited by reference to such advantages, aspects, and objects. Rather, the scope of the invention should be determined with reference to patent claims.

What is claimed:

1. A computer-implemented method, the method comprising:
   training a first neural network autoencoder to encode information of a first type into a first vector representation, the first autoencoder comprising a first encoder that maps a first input vector to the first vector representation and a first decoder that maps the first vector representation to a first output vector, where the first decoder is trained to reduce the a distance between the first output vector and the first input vector;
   training a second neural network autoencoder to encode information of a second type into a second vector representation, the second autoencoder comprising a second encoder that maps a second input vector to the second vector representation and a second decoder that maps the second vector representation to a second output vector, where the second decoder is trained to reduce a distance between the second output vector and the second input vector;
   providing a set of medical records of patient appointments;
   extracting from the medical records first portions of information of the first type and second portions of information of the second type, encoding the first portions of information with the first neural network autoencoder, and encoding the second portions of information with the second neural network autoencoder;
   generating an aggregate encoding for each medical record based on the encoded first portions of information and encoded second portions of information;
   clustering, using a machine learning clustering method, the medical records based on at least on the aggregate encodings to generate medical records clusters;
   providing an input medical record;
   extracting from the input medical record a third portion of information of the first type and a fourth portion of information of the second type, encoding the third portion of information with the first neural network autoencoder, and encoding the fourth portion of information with the second neural network autoencoder;
   generating an aggregate encoding for the input medical record based on the encoded third portion of information and encoded fourth portion of information;
   determining for the input medical record a closest medical records cluster based at least on the aggregate encoding of the input medical record;
   determining whether the input medical record is an outlier from the closest medical records cluster;
   when it is determined that the input medical record is an outlier, determining one or more features of the input medical record that cause it to be an outlier; and
   generating one or more clinical questions about the one or more determined features.

2. The computer-implemented method of claim 1, wherein the first neural network autoencoder is a variational autoencoder.

3. The computer-implemented method of claim 1, wherein the first neural network autoencoder uses Kullback-Leibler divergence.

4. The computer-implemented method of claim 1, wherein the second neural network autoencoder is a variational autoencoder.

5. The computer-implemented method of claim 1, wherein the third portion of information comprises information about one or more medications and the fourth portion of information comprises information about a diagnosis.

6. The computer-implemented method of claim 1, wherein the machine learning clustering method is k-means clustering.

7. The computer-implemented method of claim 1, further comprising determining whether the input medical record is an outlier from the closest medical records cluster by using a z-score.

8. A non-transitory computer-readable medium, the non-transitory computer-readable medium comprising instructions for:
   training a first neural network autoencoder to encode information of a first type into a first vector representation, the first autoencoder comprising a first encoder that maps a first input vector to the first vector representation and a first decoder that maps the first vector representation to a first output vector, where the first decoder is trained to reduce a distance between the first output vector and the first input vector;
   training a second neural network autoencoder to encode information of a second type into a second vector representation, the second autoencoder comprising a second encoder that maps a second input vector to the second vector representation and a second decoder that maps the second vector representation to a second output vector, where the second decoder is trained to reduce the a distance between the second output vector and the second input vector;
   providing a set of medical records of patient appointments;
   extracting from the medical records first portions of information of the first type and second portions of information of the second type, encoding the first portions of information with the first neural network autoencoder, and encoding the second portions of information with the second neural network autoencoder;
   generating an aggregate encoding for each medical record based on the encoded first portions of information and encoded second portions of information;
   clustering, using a machine learning clustering method, the medical records based at least on the aggregate encodings to generate medical records clusters;
   providing an input medical record;
   extracting from the input medical record a third portion of information of the first type and a fourth portion of information of the second type, encoding the third portion of information with the first neural network autoencoder, and encoding the fourth portion of information with the second neural network autoencoder;

generating an aggregate encoding for the input medical record based on the encoded third portion of information and encoded fourth portion of information;

determining for the input medical record a closest medical records cluster based at least on the aggregate encoding of the input medical record;

determining whether the input medical record is an outlier from the closest medical records cluster;

when it is determined that the input medical record is an outlier, determining one or more features of the input medical record that cause it to be an outlier; and generating one or more clinical questions about the one or more determined features.

9. The non-transitory computer-readable medium of claim 8, wherein the first neural network autoencoder is a variational autoencoder.

10. The non-transitory computer-readable medium of claim 8, wherein the first neural network autoencoder uses Kullback-Leibler divergence.

11. The non-transitory computer-readable medium of claim 8, wherein the second neural network autoencoder is a variational autoencoder.

12. The non-transitory computer-readable medium of claim 8, wherein the third portion of information comprises information about one or more medications and the fourth portion of information comprises information about a diagnosis.

13. The non-transitory computer-readable medium of claim 8, wherein the machine learning clustering method is k-means clustering.

14. The non-transitory computer-readable medium of claim 8, further comprising determining whether the input medical record is an outlier from the closest medical records cluster by using a z-score.

15. A computer-implemented method, the method comprising:

training a first neural network encoder to encode information of a first type into a first vector representation;

training a second neural network encoder to encode information of a second type into a second vector representation;

providing a set of medical records of patient appointments;

extracting from the medical records first portions of information of the first type and second portions of information of the second type, encoding the first portions of information with the first neural network encoder, and encoding the second portions of information with the second neural network encoder;

clustering, using a machine learning clustering method, the medical records to generate medical records clusters;

providing an input medical record;

extracting from the input medical record a third portion of information of the first type and a fourth portion of information of the second type, encoding the third portion of information with the first neural network encoder, and encoding the fourth portion of information with the second neural network encoder;

determining for the input medical record a closest medical records cluster;

determining whether the input medical record is an outlier from the closest medical records cluster;

when it is determined that the input medical record is an outlier, determining one or more features of the input medical record that cause it to be an outlier; and generating one or more clinical questions about the one or more determined features.

16. The computer-implemented method of claim 15, wherein the first neural network encoder is a variational autoencoder.

17. The computer-implemented method of claim 15, wherein the first neural network encoder uses Kullback-Leibler divergence.

18. The computer-implemented method of claim 15, wherein the second neural network encoder is a variational autoencoder.

19. The computer-implemented method of claim 15, wherein the third portion of information comprises information about one or more medications and the fourth portion of information comprises information about a diagnosis.

20. The computer-implemented method of claim 15, wherein the machine learning clustering method is k-means clustering.

21. The computer-implemented method of claim 15, further comprising determining whether the input medical record is an outlier from the closest medical records cluster by using a z-score.

22. A non-transitory computer-readable medium, the non-transitory computer-readable medium comprising instructions for:

training a first neural network encoder to encode information of a first type into a first vector representation;

training a second neural network encoder to encode information of a second type into a second vector representation;

providing a set of medical records of patient appointments;

extracting from the medical records first portions of information of the first type and second portions of information of the second type, encoding the first portions of information with the first neural network encoder, and encoding the second portions of information with the second neural network encoder;

clustering, using a machine learning clustering method, the medical records to generate medical records clusters;

providing an input medical record;

extracting from the input medical record a third portion of information of the first type and a fourth portion of information of the second type, encoding the third portion of information with the first neural network encoder, and encoding the fourth portion of information with the second neural network encoder;

determining for the input medical record a closest medical records cluster;

determining whether the input medical record is an outlier from the closest medical records cluster;

when it is determined that the input medical record is an outlier, determining one or more features of the input medical record that cause it to be an outlier; and generating one or more clinical questions about the one or more determined features.

23. The non-transitory computer-readable medium of claim 22, wherein the first neural network encoder is a variational autoencoder.

24. The non-transitory computer-readable medium of claim 22, wherein the first neural network encoder uses Kullback-Leibler divergence.

25. The non-transitory computer-readable medium of claim 22, wherein the second neural network encoder is a variational autoencoder.

26. The non-transitory computer-readable medium of claim 22, wherein the third portion of information comprises information about one or more medications and the fourth portion of information comprises information about a diagnosis.

27. The non-transitory computer-readable medium of claim 22, wherein the machine learning clustering method is k-means clustering.

28. The non-transitory computer-readable medium of claim 22, further comprising determining whether the input medical record is an outlier from the closest medical records cluster by using a z-score.

* * * * *